US00PP14244P39

(12) United States Plant Patent
Bessho

(10) Patent No.: US PP14,244 P3
(45) Date of Patent: Oct. 21, 2003

(54) CALIBRACHOA PLANT NAMED 'KAKEGAWA S44'

(50) Latin Name: *Calibrachoa*
Varietal Denomination: Kakegawa S44

(75) Inventor: Masao Bessho, Kakegawa (JP)

(73) Assignee: Sakata Seed Corporation, Yokohoma (JP)

( * ) Notice: Subject to any disclaimer, the term of this patent is extended or adjusted under 35 U.S.C. 154(b) by 0 days.

(21) Appl. No.: 10/058,775

(22) Filed: Jan. 30, 2002

(65) Prior Publication Data

US 2003/0145362 P1 Jul. 31, 2003

(51) Int. Cl.[7] ..... A01H 5/00
(52) U.S. Cl. ..... Plt./263
(58) Field of Search ..... Plt./263, 356

*Primary Examiner*—Bruce R. Campell
*Assistant Examiner*—Annette Para
(74) *Attorney, Agent, or Firm*—Jondle & Associates P.C.

(57) ABSTRACT

'Kakegawa S44' is a new variety of Calibrachoa. This new variety has lavender colored flowers and dark green foliage.

1 Drawing Sheet

BACKGROUND OF THE INVENTION

'Kakegawa S44' originated from a hybridization made in spring 1995 at Kakegawa, Japan. The female parent was the commercial variety Liricashower Rose (U.S. Plant Pat. No. 9,884). The male parent was a breeding line obtained from a commercial market in Brazil and was known only as line C-13CDE (Not patented). Seed from this cross was sown in spring 1996 and three $F_1$ plants were selected with rose colored flowers. The three selections were intercrossed and the resulting seed bulked together to produce $F_2$ seed. In spring 1997 the $F_2$ seed was sown and one plant, designated as line SK7-1169, was selected. This line was vegetatively propagated in fall 1997 and all progeny were stable and uniform. In spring 1998 the line was vegetatively propagated and cuttings were delivered to Salinas, Calif. The new variety was vegetatively propagated again in spring 1999. In these three vegetative generations the line was evaluated and determined that the traits were firmly fixed and stable. No inherent variation or off-types have been identified.

Description of the Genus Calibrachoa Llave & Lex.

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of several species classified as Petunia. These studies discovered that P. hybrida and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The base of the cuttings were dipped for 1 to 2 seconds in a 1:9 solution of Dip 'N Grow (1 part solution to 9 parts water) root inducing solution immediately prior to sticking into the cell trays. Cuttings were put into plastic cell trays having 98 cells, and containing a peat moss-based growing medium. The cuttings were misted with water from overhead for 10 seconds every 30 minutes until sufficient roots were formed. The vegetative cuttings were propagated in five to six weeks.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24C.

BRIEF DESCRIPTION OF DRAWINGS

The accompanying drawings serve by color photographic means to illustrate the new plant variety, 'Kakegawa S44'. The colors are represented as true as possible using conventional photographic procedures.

DETAILED DESCRIPTION OF THE NEW PLANT

Figure 1:
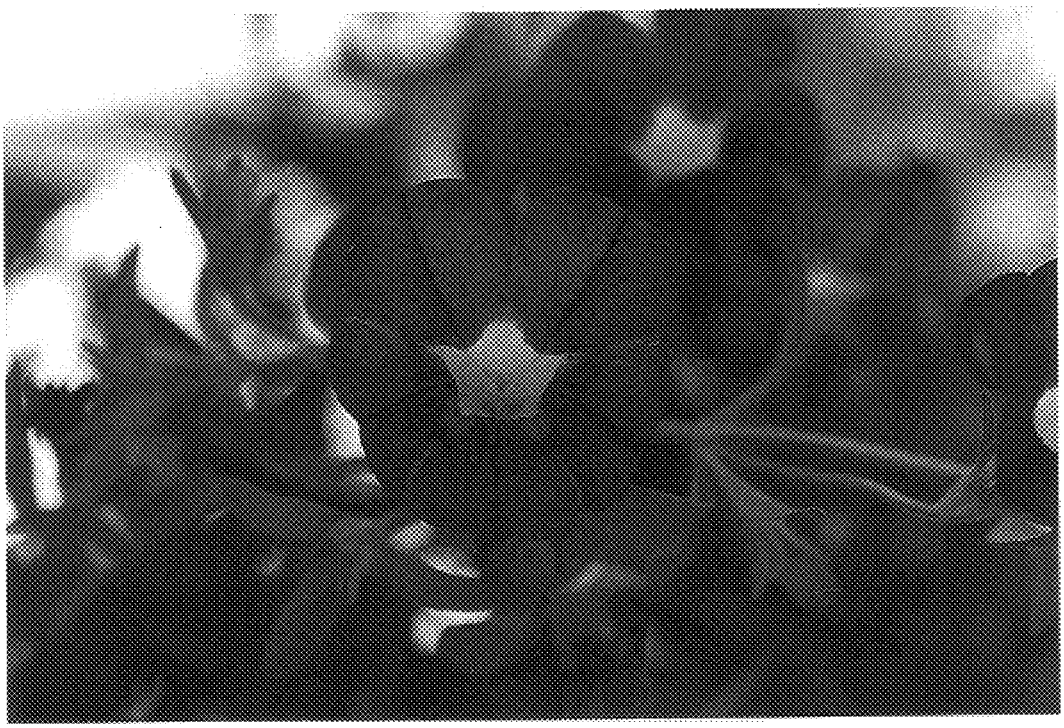
FIG. 1 is a close-up view of a 'Kakegawa S44' flower illustrating its color and shape.
Figure 2:
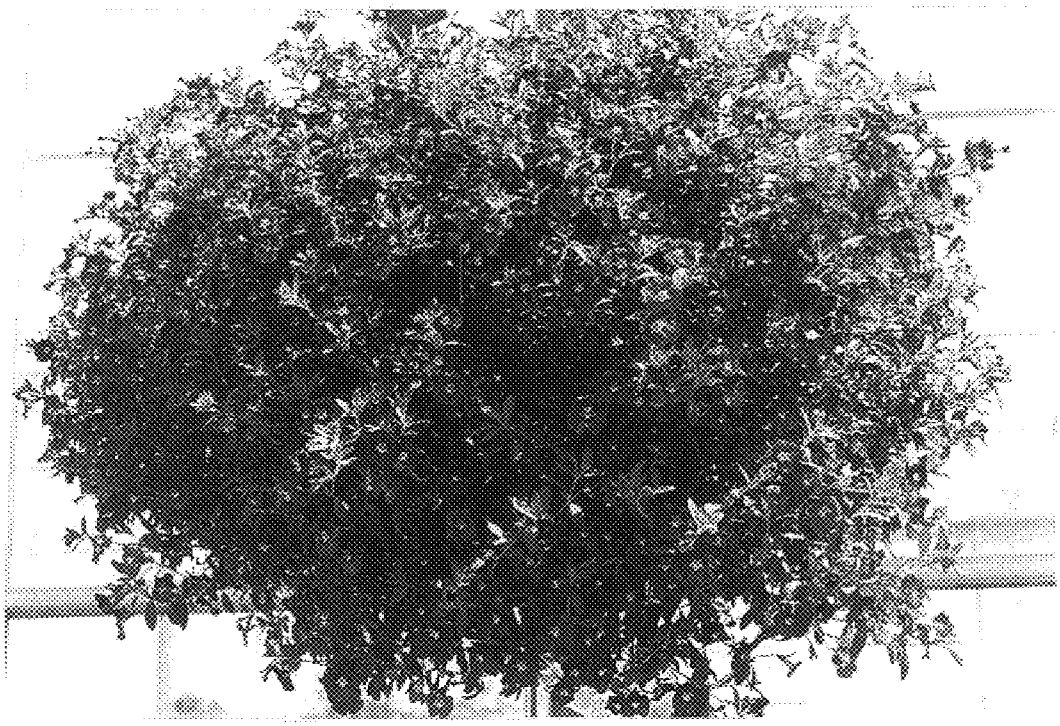
FIG. 2 is a view of several plants of the new cultivar growing in a hanging basket pot.

The following traits and characteristics describe the new variety. The observed plants were 3 months old from a rooted cutting.

Classification:

*Family.*—Solanaceae.
*Species.*—Calibrachoa spp.
*Common names.*—Petunia.

Parentage: 'Kakegawa S44' is a third generation selection from mass selection and intercrossing of prograny from the hybridization of 'Liricashower Rose' (U.S. Plant Pat. No. 9,884) and breeding line 'C-13D'.

Growth:

*Habit.*—decumbent, mounding in center.
*Height.*—23.0 cm.
*Spread.*—115.0 cm when grown in a 41 cm hanging basket or pot, and using five 20 cm potted plants in one hanging basket.
*Life cycle.*—annual.
*Time to produce a rooted cutting.*—3 weeks.
*Time to bloom from propagation.*—10 weeks.
*Flowering season.*—spring and summer.
*Flowering requirements.*—air temperatures of 13–15 C. during the night and 13–20 C. during the day; day neutral light requirement.
*Resistance/susceptibility.*—excellent resistance to rain, heat and drought; will not tolerate temperatures below 10 C.
*Form.*—branching, dense.

Stems:

*Stem color.*—R.H.S. 144B (yellow-green).
*Anthocyanin color.*—R.H.S. 77A (purple).
*Pubescence.*—heavy.
*Pubescence color.*—R.H.S. 155D (white).
*Pubescence shape.*—Pointed.
*Stem description.*—Round, ancipital.
*Stem diameter.*—2.0 mm.
*Internode length.*—1.5 to 2.5 cm.

Leaves:

*Leaf tip.*—Mucronate.
*Leaf arrangement.*—Alternate.
*Leaf base.*—Decurrent.
*Leaf color.*—Upper surface: R.H.S. 137A (green); lower surface: R.H.S. 138B (green).
*Leaf edge.*—Entire.
*Leaf fragrance.*—Absent.
*Leaf surface.*—Rough.
*Leaf surface pubescence.*—Slightly.
*Petiole color.*—R.H.S. 138B (green).
*Petiole length.*—2.0 mm.
*Leaf length.*—3.0 cm.
*Leaf shape.*—Elliptical.
*Leaf width.*—1.0 cm.

Flowers:

*Calyx.*—5 sepals; 8.0×2.0 mm (l×w); free.
*Corolla.*—5 petals, fused.
*Flower diameter.*—3.0 cm.
*Bud color.*—R.H.S. N144D (yellow-green).
*Bud shape.*—Ovate.
*Bud surface.*—Pubescent.
*Duration of flower life.*—5 days.
*Flowering habit.*—Indeterminate.
*Ovary.*—Superior.
*Placenta arrangement.*—Central.
*Peduncle size.*—2.5 cm×1.0 mm (l×w); slightly smooth, short pubescence.
*Inflorescence type.*—Solitary.
*Stamens.*—5 stamens, three short and two long, free.
*Stamens color.*—R.H.S. 144D (yellow-green).
*Stigma color.*—R.H.S. 134A (green).
*Style color.*—R.H.S. 144D (yellow-green).
*Petal size.*—3.0×1.5 cm (l×w).
*Petal pubescence.*—Glabrous.
*Petal color.*—Upper surface: R.H.S. N81B (purple-violet); lower surface: R.H.S. N81D (purple-violet); corolla tube: inner surface R.H.S. 13A (yellow); outer surface R.H.S. 3C (yellow) with R.H.S. N 77A (purple) veins.
*Pollen color.*—R.H.S. 1A (green-yellow).
*Produces seed.*—No.

'Kakegawa S44' is most similar to the variety 'Colorburst Violet' (U.S. Plant Pat. No. 12,086). The two varieties are similar in foliage, plant habit and flower size. The two plants are different because 'Colorburst Violet' has purple flowers while 'Kakegawa S44' has lavender flowers. Shown below in Table one are comparisons with the parental cultivar.

TABLE 1

| | |
|---|---|
| Parents | Liricashowe Rose & C-13D |
| Plant Habit | Female decumbent, S44 decumbent and mounding in center |
| Flower Color | Female purplish rose, S44 purple |
| Flower Size (diameter) | Female and S44 are 2.5–3.0 cm |
| Stem Pubescence | Female slight, S44 heavy |
| Stem Thickness | Female 1.0–1.5 mm (laterals), S44 2.0 mm |
| Leaf Color (upper) | Female grayish green (RHS 137B), S44 darker green (RHS 137A) |
| Leaf Pubescence | Female and S44 is slight |
| Leaf Shape | Female slightly oblanceolate; S44 is elliptical |

PLANT DISEASE AND PEST RESISTANCE

Excellent resistance to rain, heat and drought. Will not tolerate temperatures below 10 C. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepitopdera.

What is claimed is:

1. A new and distinct Calibrachoa plant as shown and described herein.

* * * * *